United States Patent [19]

Egan et al.

[11] 4,263,177

[45] Apr. 21, 1981

[54] AMINE OXIDE FOAM STABILIZERS FOR ALKYL BENZENE SULFONATE FOAMING AGENTS

[75] Inventors: Richard R. Egan, Worthington; Michelle M. Watts, Columbus, both of Ohio

[73] Assignee: Sherex Chemical Company, Inc., Dublin, Ohio

[21] Appl. No.: 52,665

[22] Filed: Jun. 27, 1979

[51] Int. Cl.³ .............. C07C 93/02; C11D 3/30; B01J 13/00

[52] U.S. Cl. .............. 252/547; 252/307; 564/297

[58] Field of Search .............. 252/547, 307; 260/584 C, 584 B

[56] References Cited

U.S. PATENT DOCUMENTS

| | | | |
|---|---|---|---|
| 3,317,430 | 5/1967 | Priestley et al. | 252/547 |
| 3,341,459 | 9/1967 | Davis | 252/547 X |
| 3,402,128 | 9/1968 | Puchta et al. | 252/547 X |
| 3,449,430 | 6/1969 | Dohr et al. | 260/583 D |
| 3,449,431 | 6/1969 | Swenson | 260/584 B |
| 3,456,012 | 7/1969 | Swenson | 260/584 B |

Primary Examiner—Harris A. Pitlick
Attorney, Agent, or Firm—Jerry K. Mueller, Jr.; Gerald L. Smith

[57] ABSTRACT

Disclosed is an amine oxide foam stabilizer for stabilizing a foam of an alkyl benzene sulfonate foaming agent, wherein said amine oxide foam stabilizer is represented by the following general structure:

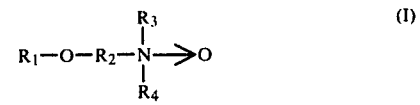

(I)

where,
$R_1$ is a $C_4$–$C_{11}$ alkyl group
$R_2$ is a $C_2$–$C_4$ alkylene group
$R_3$, $R_4$ each, independently, is a $C_1$–$C_4$ hydroxyalkyl group.

35 Claims, 2 Drawing Figures

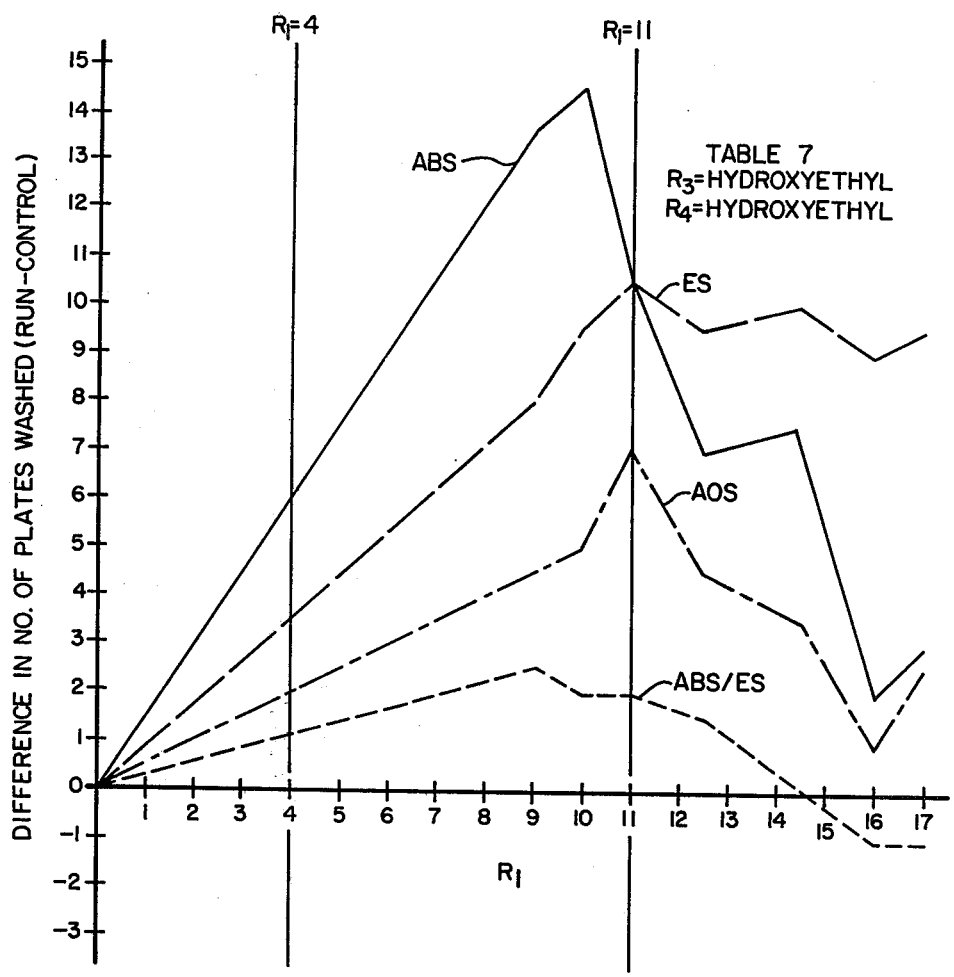

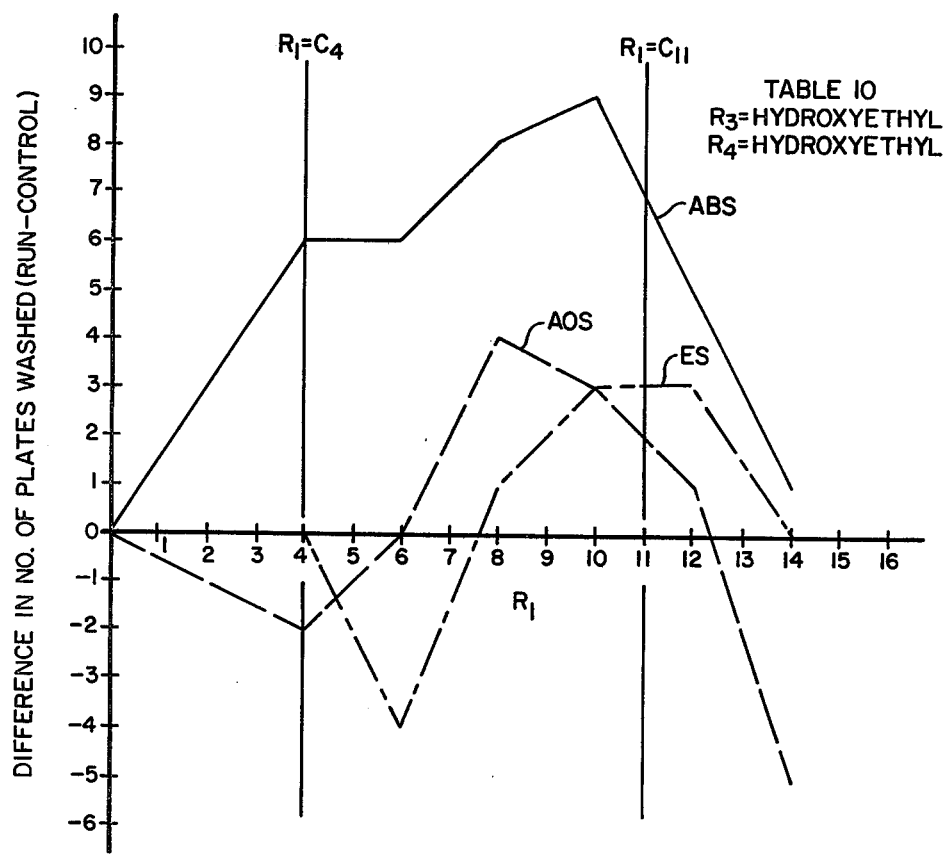

AMINE OXIDE FOAM STABILIZERS FOR ALKYL BENZENE SULFONATE FOAMING AGENTS

BACKGROUND OF THE INVENTION

The present invention relates to foam stabilizers and more particularly to a new amine oxide foam stabilizer especially efficient for stabilizing foams containing alkyl benzene sulfonate foaming agents.

Until the early 1930's, cleaning products, such as those used for cleaning clothes, washing dishes, shampooing hair and bathing, were invariably based upon fatty acid soaps (e.g. alkali metal or amine salts of fatty acids). These soaps had the ability to provide excellent cleaning and high foaming or lathering properties when used in distilled or soft water; however, in hard water containing significant concentrations of calcium and/or magnesium ions (e.g. 50-300 ppm), insoluble soaps would form which prevented the cleaning action from taking place and prevented foaming until all of the calcium and/or magnesium ions had precipitated out of the water. Besides leaving unacceptable deposits on clothing or hair, for example, the insoluble soaps resulted in a great waste of the fatty acid soap detergents. In the early 1930's, fatty alcohol sulfates, particularly sodium lauryl sulfate, were developed for this market. These anionic surface active agents give high flask foams and unlike the the fatty acid soaps which they replaced such anionic surface active agents are not affected by hard water in that no insoluble precipitates develop and their initial foaming properties are unaffected in hard water.

Fatty alcohol sulfates, however, have two major problems. The first is that the excellent initial foam is not stable and tends to collapse quickly during use. The second is that the fatty alcohol sulfates are expensive. The first problem can be overcome by employing a foam stabilizer in the formulations for extending the foam life. The second problem necessitated development of alternative anionic surfactants. An example of a much lower cost anionic surface active agent having high initial foam in hard water is an alkyl benzene sulfonate (for example, sodium dodecyl benzene sulfonate). Another lower cost anionic surface active agent which gives high flash foams in hard water is an alpha olefin sulfonate (for example, sodium dodecyl sulfonate). Both of these latter, lower cost anionic surface active agents require a foam stabilizer for extending the life of the foam in use.

Heretofore, foam stabilizers generally were alkanolamides and amine oxides. Both the alkanolamides and the amine oxides typically are synthesized from long-chain fatty molecules which are derived from, for example, lauric-containing triglyceride oils such as coconut oil or palm kernel oil. Typical present day, commercially used alkanolamide foam stabilizers include, for example, lauric or coco monoethanolamide, lauric or coco diethanol amide, and lauric or coco isopropanolamide; and amine oxides include, for example, lauryl or coco dimethylamine oxide, lauryl or coco bis(2-hydroxyethyl)amine oxide, lauryl or coco beta-hydroxydimethyl amine oxide, and lauryl or coco beta-hydroxy bis (2-hydroxyethyl) amine oxide. Further amine oxide foam stabilizers can be found in U.S. Pat. Nos. 3,449,430, 3,449,431, and 3,456,012.

The amine oxides function well as foam stabilizers for fatty alcohol sulfates, fatty ether alcohol sulfates, reasonably well for alpha olefin sulfonates, but not for alkyl benzene sulfonates. The alkanolamides function well for all of the above-listed anionic surfactants; however, the alkanolamides tend to be irritating to the skin and eye, and many are difficult to handle and store practically.

BROAD STATEMENT OF THE INVENTION

The present invention is a foam stabilizer for stabilizing a foam of an alkyl benzene sulfonate foaming agent. The foam stabilizer is characterized by an amine oxide foam stabilizer represented by the following general structure:

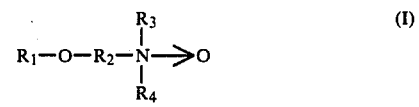

where,
$R_1$ is a $C_4$-$C_{11}$ alkyl group
$R_2$ is a $C_2$-$C_4$ alkylene group
$R_3$, $R_4$ each, independently is a $C_1$-$C_4$ hydroxyalkyl group.

Another aspect of the invention is a stabilized alkyl benzene sulfonate foaming agent which is characterized by a combination of an alkyl benzene sulfonate foaming agent and the amine oxide foam stabilizer represented by structure (I) above. A further aspect of the present invention is a water soluble foamable composition which includes an alkyl benzene sulfonate foaming agent. The improvement in such foamable composition is characterized by the presence of an amine oxide foam stabilizer represented by structure (I) above. A still further aspect of the present invention is a process for making a water-soluble foamable composition which includes an alkyl benzene sulfonate foaming agent. The improvement in process is characterized by adding to said composition a foam-stabilizing effective proportion of an amine oxide foam stabilizer represented by structure (I) above.

Advantages of the present invention include that the amine oxide foam stabilizers are relatively low in cost to prepare and are remarkably effective in stabilizing a foam of an alkyl benzene sulfonate foaming agent. Also, the disclosed amine oxide foam stabilizers provide systems which are milder than those which are stabilized by an alkanolamide in that the amine oxides disclosed herein provide substantially less irritation to the skin and eye in such systems. Further, the amine oxide foam stabilizers can be used in systems ranging from liquid and powdered detergent systems for cleaning clothes, and liquid diswashing formulations and fine fabric detergent formulations, in bubble baths, in hair shampoos, in hair cream rinses, and in a wide variety of other uses.

BRIEF DESCRIPTION OF THE DRAWINGS

FIGS. 1 and 2 display graphically the results obtained in dishwashing tests reported and described in the Examples. A detailed description of the drawings is given in connection with the Examples which follow.

DETAILED DESCRIPTION OF THE INVENTION

The amine oxide foam stabilizers of the present invention are represented by the following general structure:

$$R_1-O-R_2-\underset{R_4}{\overset{R_3}{N}}\rightarrow O \quad (I)$$

In structure (I), $R_2$ is a $C_2$-$C_4$ alkylene group; and preferably a propylene group, $R_3$ and $R_4$ each, independently, is a $C_1$-$C_4$ hydroxyalkyl group and preferably a hydroxyethyl or hydroxypropyl group; and $R_1$ is a $C_4$-$C_{11}$ alkyl group. The $R_1$ substituent group of the amine oxide in structure (I) is of critical importance in the amine oxide foam stabilizer displaying effectiveness or functionality in stabilizing foams of alkyl benzene sulfonate foaming agents. The $R_1$ group preferably is a straight chain alkyl group with optional moderate methyl or hydroxyl substitution. Preferably, such methyl substitution should be limited to at most about 25% by weight of the $R_1$ group, and only very light hydroxyl substitution should be present. Branching of the $R_1$ group distinctly disfavors the amine oxide from displaying effective foam stabilizing characteristics with respect to alkyl benzene sulfonate foaming agents.

Similarly, the $R_4$ and $R_3$ substituents are restricted to lower hydroxyalkyl groups due to the quite unexpected discovery that lower alkyl groups (as the $R_4$ and $R_3$ substituents) cause loss of activity or functionality of the amine oxide even though the $R_1$ group restriction is adhered to. While the disclosed amine oxide foam stabilizers do function somewhat with foaming agents of ether sulfates and alpha-olefin sulfonates, for example, as would be expected; unexpectedly, however, research on the present invention resulted in the discovery that such amine oxides are highly functional and very effectively stabilize foams of alkyl benzene sulfonate foaming agents provided that the $R_1$ group limitation and the $R_4$, $R_3$ group limitations are strictly adhered to. The unusually good functionality of the disclosed amine oxides in stabilizing foams of alkyl benzene sulfonate foaming agents is unexpected because no amine oxide is reported in the literature to be functional for stabilizing foams of alkyl benzene sulfonate foaming agents and because the amine oxides disclosed herein are functional at relatively shorter $R_1$ chain lengths than those amine oxides presently used as foam stabilizers and the $R_4$, $R_3$ substituents cannot be mere alkyl groups but must be hydroxyalkyl groups. For example, typical present-day formulations for dishwashing detergents and shampoos, for example, employ alkanolamides and amine oxides, such as those listed above, as foam stabilizers. Typical formulations utilizing such prior foam stabilizers are listed below.

TABLE 1

| TYPICAL CONVENTIONAL PRODUCT FORMULATIONS | | | |
|---|---|---|---|
| | FORMULATION NUMBER (% by weight) | | |
| | #1 | #2 | #3 |
| Liquid Dishwash Formulations | | | |
| Anionic Surfactants | | | |
| Ammonium Lauryl Ether Sulfate | — | 20 | 15 |
| Sodium Dodecyl Benzene Sulfonate | 25 | — | 10 |
| Foam Stabilizers | | | |
| Lauric or Coco Diethanolamide | 5 | — | — |
| Lauryl or Coco Dimethyl Amine Oxide | — | 5 | 5 |
| Nonionic Surfactants | | | |
| Ethoxylated Nonyl Phenol | | | |
| (9 or 10 ethoxy groups) | 10 | — | — |
| Ethoxylated $C_{12}C_{14}$ alcohols | | | |
| (7 or 12 ethoxy groups) | — | — | 5 |
| Coupling Agents | | | |
| Sodium Xylene Sulfonate | 0-5 | 0-5 | 0-5 |
| Ethanol | 0-5 | 0-5 | 0-5 |
| Diluent-Water | Balance | Balance | Balance |
| Colorants, Emollients & Perfumants added to suit | | | |
| Liquid Shampoo Formulations | | | |
| Anionic Surfactants | | | |
| Ammonium Lauryl Sulfate | 16 | — | — |
| Sodium Lauryl Sulfate | — | 16 | — |
| Sodium Lauryl Ether Sulfate | — | — | 16 |
| Foam Stabilizers | | | |
| Lauryl or Coco Diethanolamide | — | 4 | — |
| Lauryl or Coco Dimethyl Amine Oxide | 4 | — | 4 |
| Diluent Water | 80 | 80 | 80 |

Special emollients and hair conditioners may be added to suit along with perfumants and colorants.

Thus, generally $C_{12}$ and higher $R_1$ groups predominate in use for such amine oxide stabilizers; yet, this is not the case for effectively stabilizing alkyl benzene sulfonate foams as the examples will amply demonstrate.

Synthesis of amine oxide foam stabilizers is routine and generally involves the reaction of a suitable tertiary amine with a peroxidizing agent, preferably hydrogen peroxide, at temperatures of about 60° to 80° C. Peracids also can be important reagents for this synthesis (see March, *Advanced Organic Chemistry*, Second Edition, page 1111, McGraw Hill, Inc., New York, New York, 1977). Synthesis of the tertiary amines which can be converted into the amine oxide foam stabilizers is conventional. For example, an alcohol can be subjected to a conventional cyanoalkylation reaction with subsequent catalytic hydrogenation for forming a primary ether amine. The starting alcohol contains the $R_1$ group from structure (I) and accordingly preferably is a primary alcohol of relatively straight chain containing optional moderate methyl substitution. The ether amine resulting from the cyanoalkylation reaction can be treated in several ways for forming the desired amine oxides foam stabilizer. A preferable treatment involves the reaction of a $C_2$-$C_4$ alkylene oxide to the primary ether amine for forming a tertiary ether amine containing hydroxyalkyl groups. Mixtures of the alkylene oxide reactants can be used as is necessary, desirable, or convenient. The resulting tertiary amine then can be reacted with hydrogen peroxide or a peracid for forming the amine oxide.

The alkyl benzene sulfonate foaming agents which the amine oxides stabilize effectively are conventional in composition and typically are dodecyl and tridecyl benzene sulfonates. Other conventional alkyl benzene sulfonates, however, which find use in foamable compositions likewise can be effectively stabilized by the amine oxides of the present invention. Typically, the alkyl benzene sulfonates are formed into alkali metal, alkaline earth metal, or amine salts for use in foamble compositions as is practiced in present day commercial use of alkyl benzene sulfonate foaming agents. The proportion of alkyl benzene sulfonate foaming agent used is conventional according to the particular formulation of interest, such as those typical product formulations described above.

Depending upon the particular product being made, a variety of additives such as cosolvents (for example, alcohols), colorants, perfumants, emollients, conditioners, and the like can be included in the formulation. Typical foamable compositions comprehended for use with the alkyl benzene sulfonate and amine oxides of the present invention include dishwashing and clothes detergents, hair shampoos, hair cream rinses, and the like. Such products can be in the form of liquids, gels, or powders as is well known to those skilled in the art. Compounding of the formulations can be practiced in conventional fashion and little more need be said about it here.

The following examples show in detail how the present invention can be practiced but should not be construed as limiting. In this applicaion, all temperatures are in degrees Centigrade, all percentages and proportions are by weight, and all units are in the metric system, unless otherwise expressly indicated.

IN THE EXAMPLES

For convenience several abbreviations are used in the examples. A list of these abbreviations and the term for which they stand are given below.
Me = methyl group
EO = hydroxy ethyl group
PO = hydroxy propyl group
BO = hydroxy butyl group
2-EH = 2-hydroxy ethyl group
ABS = sodium dodecylbenzene sulfonate
ES = sodium or ammonium lauryl ether sulfate
AOS = sodium myristyl/palmityl sulfonate The substituent R groups of the amide oxide foam stabilizer candidates evaluated conform to structure (I) and are designated by the number of carbon atoms in each group in the tables. Note that $C_{13}(b)$ is a highly branched tridecyl group. Also, in some instances mixtures of primary alcohols were used in the amine oxide synthesis and, thus, a mixture of amine oxides having varying $R_1$ groups resulted. This situation is indicated by a range of carbon atoms for the $R_1$ group in the tables.

Also, Ross-Miles foam tests (1% amine oxide by weight) were conducted in accordance with ASTM D 1173 at 23° C. using deionized water (identified as Soft Water in the tables) and water containing 150 ppm calcium and magnesium salts (simulated Hard Water, identified as Hard Water in the tables). Foam heights were measured and recorded in millimeters initially ($T_0$ in the tables) and after 5 minutes ($T_5$ in the tables).

The surface tension tests (identified as Surface Tension in the tables) are reported in dynes/cm. for 0.025% by weight amine oxide in water and were conducted at 25° C. in accordance with ASTM D 1331-56 (surface tension of water being 72.3 dynes/cm). The interfacial tension tests (identified as Interfacial Tension in the tables) are reported in dynes/cm for 0.025% by weight amine oxide in a water layer adjacent a Nujol oil (a mineral oil) layer and were conducted at 25° C. in accordance with ASTM D 1331-56 (interfacial tension of water/Nujol being 31.3 dynes/cm). Deionized water was used in both the surface tension and interfacial tension tests. The amine oxide foam stabilizer candidates evaluated in the examples were synthesized by reacting a primary alcohol with acrylonitrile (a cyanoethylation reaction) followed by catalytic hydrogenation to form a primary ether amine. For production of a tertiary amine containing hydroxyalkyl groups, the primary amine was reacted further with butylene oxide, ethylene oxide, propylene oxide, or a 3:1 molar ratio respectively of ethylene oxide and propylene oxide. For production of a tertiary amine containing alkyl groups, the primary amine was subjected to a reductive methylation reaction by further reaction with formaldehyde and hydrogen. For both synthesis schemes, the resulting tertiary amine then was reacted with hydrogen peroxide for conversion of the tertiary amine into the corresponding amine oxide.

Dishwashing tests were conducted in accordance with the following procedure. White semi-porcelin plates (22.86 cm. in diameter) are soiled the day prior to use by smearing 5 ml. of melted Light Spry shortening evenly over each plate with a 5.08 cm. paint brush. Soil is dispensed by a Beckman dispenser. A blue dye (Calico Oil Blue V from American Cyanamid) is added to the soil to make residual soil easier to visually perceive during the tests.

For the tests, three operators and 4 dish wash tubs (about 38.1 cm. top diameter, 29.21 cm. bottom diameter, and 21.59 cm. deep) are used. Twenty ml of a 15,000 ppm hard water standard is added to each dish tub followed by the addition of 6 liters of deionized water at 48° C. Sixteen grams of the dishwashing liquid is weighed into a clear beaker and transferred quantitatively to a tub. Each tub contains a different dishwashing detergent formulation. Each tub is agitated with an electric mixer for 25 seconds (¾ immersion of the beaters at maximum speed setting). Two of the presoiled plates then are washed by one of the three operators at each tub. The operators then rotate from tub to tub in a counterclockwise movement each two plates. Disposable towels are used to wash the plates. Washing is continued until the end-point is reached. The end-point is defined as the first permanent break in the foam. The number of plates washed in each tub to the foam endpoint is counted and recorded. The more dishes washed before the foam breaks, the more effective the foam stabilizer.

EXAMPLE 1

500 Grams of a $C_8$–$C_{10}$ alcohol mixture (3.57 moles) was added to a 1 liter 3-neck flask equipped with a stirrer, a thermometer, and a funnel. 2.5 Grams of sodium methylate was added to the alcohol and stirring begun. 208 grams (3.93 moles) of acrylonitrile was added to the dropping funnel. The acrylonitrile was added to the alcohol with constant stirring at a rate to maintain the temperature at about 49°–52° C. throughout the reaction. When all of the acrylonitrile had been added, the sodium methylate was neutralized with 2.7 grams of glacial acetic acid. The resulting nitrile then was washed twice with 100 milliliter portions of water and vacuum dried. The yield was 650 rams or approximately 92% of theoretical.

650 Grams (3.36 moles) of the ether nitrile from above is added to a Parr bomb along with 6.5 grams of Raney mud 31-169 catalyst. The reactor was sealed and raised to a pressure of 300 psig with ammonia and warmed to a temperature of about 138°–149° C. Hydrogen then was added at such a rate to maintain the total pressure of 500–550 psig. The reaction required approximately 2–4 hours. The bomb was cooled and then filtered free of catalyst. The yield was approximately 635 grams or 96% of theoretical.

600 Grams of the ether amine (3.04 moles) was placed into a Parr bomb. The bomb then was sealed and swept with nitrogen to remove all oxygen and traces of moisture. The product was vacuum stripped for 15 minutes and then nitrogen was introduced into the reactor to a pressure of 5 psig. The temperature was elevated to about 149°–163° C. The addition of ethylene oxide then was begun. A total of 272 grams of ethylene oxide (6.2 moles) was added to the system. The ethylene oxide was added at a rate to allow the total guage pressure to rise to between 45 and 50 psi while maintaining a temperature of about 163°–177° C. The alkoxylation reaction required approximately 3-4 hours. The yield was 850 grams or approximately 98% of theoretical.

800 grams (2.8 moles) of the ethoxy ether amine and 1114 grams of water were added to a 2 liter three necked flask equipped with a thermometer, stirrer, and dropping funnel. 100.3 grams of hydrogen peroxide (2.95 moles) in water (50% $H_2O_2$ in water) was added through the dropping funnel at about 49°–55° C. The temperature was maintained in this range throughout the reaction. During the addition of the peroxide it is usually observed that a gel tends to form, but this breaks usually as the majority of the peroxide has been added. The oxidation was complete in 3-4 hours giving a yield of 2,100 grams or approximately 99% based upon the alkoxylated ether amine oxide. The resulting product is a 40% solution of the ether amine oxide in water.

EXAMPLE 2

Traditionally, in order for any compound to be an acceptable foam stabilizer such compound also must be a surface active agent (surfactant). This traditional thinking will, in part, be disproved herein. For present purposes a compound is classified as being surface active if the compound in dilute aqueous solution will lower the surface tension of water from 72.3 dynes/cm to between about 28 and 40 dynes/cm, and lower the interfacial tension of water against a refined mineral oil (Nujol oil) from 31.3 dynes/cm to below about 10 dynes/cm. Thus, several amine oxides were evaluated as to their suitability to be classified as a surface active agent.

In the following tables, it should be kept in mind that the surface tension and interfacial tensions are given in dynes/cm and that the R groups refer to structure (I) above. Table 2 displays the results obtained for amine oxides synthesized from ostensibly pure primary alcohols ($R_1$ group).

TABLE 2

| Test No | $R_1$ | $R_2$ | $R_3$ | $R_4$ | Surface Tension (dynes/cm) | Interfacial Tension (dynes/cm) |
|---|---|---|---|---|---|---|
| 3660-149 | $C_4$ | $C_3$ | Me | Me | 71.5 | 31.6 |
| 3660-138 | $C_4$ | $C_3$ | EO | EO | 70.6 | 29.9 |
| 36740-21 | $C_6$ | $C_3$ | Me | Me | 52.0 | 24.0 |
| 3674-20 | $C_6$ | $C_3$ | EO | EO | 62.0 | 24.0 |
| 3673-30 | $C_8$ | $C_3$ | Me | Me | 40.0 | 12.0 |
| 3674-35 | $C_8$ | $C_3$ | EO | EO | 42.0 | 4.5 |
| 3673-146 | $C_8$ | $C_3$ | BO | BO | 37.0 | 11.3 |
| 3660-130 | $isoC_8$ | $C_3$ | Me | Me | 33.9 | 4.4 |
| 3660-167 | $isoC_8$ | $C_3$ | EO | EO | 39.4 | 8.9 |
| 3660-119 | 2-EH | $C_3$ | Me | Me | 40.4 | 5.1 |
| 3674-39 | 2-EH | $C_3$ | EO | EO | 41.5 | 12.0 |
| 3660-191 | $C_{10}$ | $C_3$ | Me | Me | 26.0 | 10.0 |
| 3674-13 | $C_{10}$ | $C_3$ | EO | EO | 31.0 | 7.0 |
| 3660-186 | $isoC_{10}$ | $C_3$ | Me | Me | 34.0 | 8.0 |
| V-70E | $isoC_{10}$ | $C_3$ | EO | EO | 30.0 | 5.0 |
| 3674-42 | $C_{12}$ | $C_3$ | Me | Me | 28.0 | 15.0 |

TABLE 2-continued

| Test No | $R_1$ | $R_2$ | $R_3$ | $R_4$ | Surface Tension (dynes/cm) | Interfacial Tension (dynes/cm) |
|---|---|---|---|---|---|---|
| 3593-187 | $C_{12}$ | $C_3$ | EO | EO | 30.7 | 5.1 |
| 3660-162 | $C_{13(b)}$ | $C_3$ | Me | Me | 28.4 | 4.6 |
| EPO 194-128 | $C_{13(b)}$ | $C_3$ | EO | EO | 29.1 | 5.2 |
| EPO 194-131 | $C_{13}$ | $C_3$ | EO | PO | 30.0 | 9.4 |
| 3673-110 | $C_{13(b)}$ | $C_3$ | BO | BO | 49.9 | 26.8 |
| 3593-193 | $C_{14}$ | $C_3$ | EO | EO | 30.8 | 5.8 |
| 3660-6 | $C_{16}$ | $C_3$ | EO | EO | 35.4 | 10.6 |

The surface tension and interfacial tension tests were repeated for amine oxides synthesized from mixtures of ostensibly pure alcohols ($R_1$ group), so that each amine oxide was a mixture of amine oxides with varying $R_1$ groups corresponding to the alcohol mixture used in the synthesis thereof. The results obtained are displayed in Table 3.

TABLE 3

| Test No | $R_1$ | $R_2$ | $R_3$ | $R_4$ | Surface Tension (dynes/cm) | Interfacial Tension (dynes/cm) |
|---|---|---|---|---|---|---|
| 3660-147 | $C_8$-$C_{10}$ | $C_3$ | Me | Me | 32.4 | 5.9 |
| 3660-32 | $C_8$-$C_{10}$ | $C_3$ | EO | EO | 34.8 | 6.8 |
| EPO 194-135 | $C_8$-$C_{10}$ | $C_3$ | EO | PO | 34.8 | 7.5 |
| 3660-140 | $C_9$-$C_{11}$ | $C_3$ | Me | Me | 28.7 | 3.4 |
| 3660-136 | $C_9$-$C_{11}$ | $C_3$ | EO | EO | 34.0 | 10.5 |
| 3660-126 | $C_{10}$-$C_{12}$ | $C_3$ | Me | Me | 29.1 | 2.5 |
| 3478-148 | $C_{10}$-$C_{12}$ | $C_3$ | EO | EO | 33.1 | 4.0 |
| 3528-50 | $C_{10}$-$C_{12}$ | $C_3$ | PO | PO | 32.1 | 5.2 |
| EPO 194-136 | $C_{10}$-$C_{12}$ | $C_3$ | EO | PO | 32.0 | 11.8 |
| 3674-47 | $C_{12}$-$C_{13}$ | $C_3$ | Me | Me | 28.5 | 10.0 |
| 3660-39 | $C_{12}$-$C_{13}$ | $C_3$ | EO | EO | 33.9 | 7.5 |
| 3478-151 | $C_{12}$-$C_{15}$ | $C_3$ | Me | Me | 32.5 | 6.8 |
| EPO 198-48C | $C_{12}$-$C_{15}$ | $C_3$ | EO | EO | 30.7 | 3.7 |
| 3478-147 | $C_{12}$-$C_{15}$ | $C_3$ | EO | EO | 32.3 | 5.3 |
| 3528-49 | $C_{12}$-$C_{15}$ | $C_3$ | PO | PO | 29.6 | 12.0 |
| 3673-106 | $C_{12}$-$C_{15}$ | $C_3$ | BO | BO | 51.3 | 25.6 |
| EPO 198-49B | $C_{12}$-$C_{15}$ | $C_3$ | EO | PO | 30.9 | 4.0 |
| 3593-93 | $C_{14}$-$C_{15}$ | $C_3$ | EO | EO | 31.5 | 3.2 |
| 3593-120 | $C_{14}$-$C_{15}$ | $C_3$ | EO | PO | 30.1 | 3.7 |
| 3593-73 | $C_{12}$-$C_{18}$ | $C_3$ | EO | EO | 32.7 | 4.1 |
| 3593-74 | $C_{12}$-$C_{18}$ | $C_3$ | EO | PO | 31.5 | 5.1 |
| 3593-5 | $C_{14}$-$C_{18}$ | $C_3$ | EO | EO | 35.5 | 9.0 |
| 3593-129 | $C_{16}$-$C_{18}$ | $C_3$ | EO | EO | 40.0 | 13.5 |

The results tabulated in Table 3 clearly show that amine oxides containing $R_1$ groups of less than $C_8$ did not perform satisfactorily for such amine oxides to be classified as surface active agents. However, the amine oxides containing $R_1$ groups of $C_8$ and above generally did perform satisfactorily for such amine oxides to be classified as surface active agents. Also, as shown by the results tabulated Table 3, mixtures of amine oxides containing a mix of different $R_1$ groups performed satisfactorily.

Thus, the foregoing results indicate that for an amine oxide of structure (I) to be considered as a foam stabilizer, such amine oxide should have an $R_1$ group of $C_8$ and greater. However, as subsequent Examples will demonstrate, the traditional surface active criterion is not necessarily always correct.

EXAMPLE 3

Several of the amine oxides which tested satisfactorily as surface active agents were subjected to the Ross-Miles foam test in order to ascertain their ability to foam. The concentration of amine oxide in each test was 1% by weight. Foam heights of at least 180-190 mm are required in order for the amine oxide to be classified as a high foaming agent (or high foamer). Table 4 displays the results obtained.

TABLE 4

| | | | | ROSS-MILES TEST (mm) | | | |
|---|---|---|---|---|---|---|---|
| | | | | Soft Water | | Hard Water | |
| Run No. | $R_1$ | $R_2$ | $R_3$ | $R_4$ | $T_0$ | $T_5$ | $T_0$ | $T_5$ |
| 1 | $C_8$-$C_{10}$ | $C_3$ | EO | EO | 217 | 175 | 222 | 200 |
| 2 | $C_8$-$C_{10}$ | $C_3$ | EO | PO | 215 | 190 | 222 | 202 |
| 3 | iso-$C_{10}$ | $C_3$ | EO | EO | 210 | 195 | 227 | 200 |
| 4 | iso-$C_{10}$ | $C_3$ | EO | PO | 220 | 193 | 223 | 192 |
| 5 | $C_{10}$-$C_{12}$ | $C_3$ | EO | EO | 220 | 200 | 235 | 200 |
| 6 | $C_{10}$-$C_{12}$ | $C_3$ | PO | PO | 230 | 180 | 220 | 195 |
| 7 | $C_{10}$-$C_{12}$ | $C_3$ | EO | PO | 225 | 195 | 235 | 200 |
| 8 | $C_{13}$(b) | $C_3$ | EO | EO | 212 | 180 | 220 | 190 |
| 9 | $C_{13}$(b) | $C_3$ | EO | PO | 215 | 185 | 220 | 190 |
| 10 | $C_{13}$(b) | $C_3$ | BO | BO | 215 | 183 | 217 | 190 |
| 11 | $C_{12}$-$C_{15}$ | $C_3$ | EO | EO | 220 | 185 | 230 | 200 |
| 12 | $C_{12}$-$C_{15}$ | $C_3$ | EO | PO | 222 | 187 | 230 | 195 |
| 13 | $C_{12}$-$C_{15}$ | $C_3$ | PO | PO | 212 | 175 | 217 | 187 |
| 14 | $C_{12}$-$C_{15}$ | $C_3$ | BO | BO | 203 | 183 | 215 | 192 |

The foregoing tabulated results indicate that all of the amine oxides tested performed satisfactorily as high foamers regardless of the particular $R_1$ group of the amine oxide.

EXAMPLE 4

The foregoing examples demonstrate that amine oxides having an $R_1$ group of $C_8$ and higher are surface active agents and high foamers. In order to asccertain their ability to act as foam stabilizers, several amine oxides having varying $R_1$ groups (including $C_4$ and $C_6$ alkyl groups) were used in several liquid dishwashing formulations, each having a different foaming agent. The foaming agents used were sodium dodecylbenzene sulfonate (an alkylbenzene sulfonate, ABS), sodium or ammonium lauryl ether sulfate (an alkyl ether sulfate, ES) and sodium myristyl/palmityl sulfonate (an alpha-olefin sulfonate, AOS).

The dishwashing formulations used appear below.

| INGREDIENT | WEIGHT % |
|---|---|
| Amine Oxide Foam Stabilizer | 4 |
| Foaming Agent | 15 |
| Deionized Water | 81 |

The foregoing formulation uses the foaming agent at an active level which requires no cosolvent in order to adequately disperse the formulation in water to yield an acceptable viscosity of the resulting solution. Also, several commercial liquid dishwashing formulations are recommended for use at a 15% strength.

In these tests the dishwashing test described above was utilized. For Table 5, $R_3$ and $R_4$ were each a methyl group; for Table 6, $R_3$ and $R_4$ were each a hydroxyethyl group; for Table 7, $R_3$ and $R_4$ were each a hydroxyethyl group; for Table 8, $R_3$ and $R_4$ each were a methyl group; and for Table 9, $R_3$ and $R_4$ each were a hydroxyethyl group. $R_2$ was a propylene group in all tests. The results obtained appear in the following tables.

TABLE 5

| | | $R_3, R_4$ = Methyl | | | |
|---|---|---|---|---|---|
| | | No. of Plates Washed | | | |
| Run No. | $R_1$ | ABS | ES | AOS | ABS/ES |
| 1 | $C_8$-$C_{10}$ | 13 | 11 | 16 | 14 |
| 2 | $C_9$-$C_{11}$ | 13 | 13 | 16 | 18 |
| 3 | $C_{10}$-$C_{12}$ | 13 | 12 | 16 | 18 |
| 4 | $C_{12}$-$C_{13}$ | 9 | 11 | 13 | 13 |

TABLE 6

| | | $R_3, R_4$ = Hydroxyethyl | | | |
|---|---|---|---|---|---|
| | | No. of Plates Washed | | | |
| Run No. | $R_1$ | ABS | ES | AOS | ABS/ES |
| 1 | $C_4$ | 16 | 5 | 13 | 13 |
| 2 | $C_6$ | 16 | 4 | 12 | 14 |
| 3 | $C_8$ | 24 | 6 | 14 | 17 |
| 4 | $C_{10}$ | 19 | 11 | 20 | 17.5 |
| 5 | $C_{12}$ | 14 | 12 | 14 | 18 |
| 6 | $C_{14}$ | 14 | 13 | 13 | 14 |
| 7 | $C_{16}$ | 10 | 8 | 11 | 11 |

TABLE 7

| | | $R_3, R_4$ = Hydroxyethyl | | | |
|---|---|---|---|---|---|
| | | No. of Plates Washed | | | |
| Run No. | $R_1$ | ABS | ES | AOS | ABS/ES |
| Control | | 9.0 | 4.0 | 11.0 | 13.0 |
| 1 | $C_8$-$C_{10}$ | 22.7 | 12.0 | 15.5 | 15.5 |
| 2 | $C_9$-$C_{11}$ | 23.5 | 13.5 | 16.0 | 15.0 |
| 3 | $C_{10}$-$C_{12}$ | 19.5 | 14.5 | 18.0 | 15.0 |
| 4 | $C_{12}$-$C_{13}$ | 16.0 | 13.5 | 15.5 | 14.5 |
| 5 | $C_{14}$-$C_{15}$ | 16.5 | 14.0 | 14.5 | 13.0 |
| 6 | $C_{14}$-$C_{18}$ | 11.0 | 13.0 | 12.0 | 12.0 |
| 7 | $C_{16}$-$C_{18}$ | 12.0 | 13.5 | 13.5 | 12.0 |

TABLE 8

| | | $R_3, R_4$ = Methyl | | | |
|---|---|---|---|---|---|
| | | No. of Plates Washed | | | |
| Run No. | $R_1$ | ABS | ES | AOS | ABS/ES |
| Control | | 10 | 5 | 11.5 | 11.5 |
| 1 | iso-$C_8$ | 14 | 9 | 12 | 11 |
| 2 | 2-EH | 13 | 7 | 12 | 12 |
| 3 | iso$C_{10}$ | 15 | 9 | 16 | 13 |
| 4 | $C_{13}$(b) | 10 | 13 | 12 | 12 |

TABLE 9

| | | $R_3, R_4$ = Hydroxyethyl | | | |
|---|---|---|---|---|---|
| | | No. of Plates Washed | | | |
| Run No. | $R_1$ | ABS | ES | AOS | ABS/ES |
| 1 | iso-$C_8$ | 15 | 6 | 10 | 13 |
| 2 | 2-EH | 15 | 6 | 15 | 12 |
| 3 | iso-$C_{10}$ | 14 | 8 | 13 | 14 |
| 4 | $C_{13}$(b) | 11 | 9 | 13 | 14 |

The above-tabulated results show several interesting and unexpected features of the present invention. Initially, it should be noted that the results reported in Tables 8 and 9 clearly show that the amine oxides tested functioned only slightly for all foaming agents with $R_1$ being branched. This is true whether $R_3$, $R_4$ are alkyl groups or hydroxyalkyl groups. The next (quite unexpected) result seen from the results reported in Table 5 is that with $R_3$, $R_4$ both being methyl groups (an alkyl group) the amine oxide functioned only slightly with all of the foaming agents even though $R_1$ was within the preferred range of $C_8$-$C_{11}$ alkyl groups.

Next, the results reported in Tables 6 and 7 show at least three unexpected results. The first is that when $R_1$ is greater than a $C_{11}$ group (e.g. $C_{12}$–$C_{18}$ alkyl groups), the amine oxide functioned only moderately as a foam stabilizer for all foaming agents. The second is that within the range of $R_1 = C_4$–$C_{11}$ alkyl groups, the amine oxide functioned exceptionally well for the ABS foaming agent with $R_3$ and $R_4$ being hydroxyalkyl groups. This functionality was more pronounced with the ABS foaming agent than with the other foaming agents wherein the amine oxide functioned only slightly to stabilize the foams. The third, and perhaps the most unexpected result is that the amine oxides containing $C_4$–$C_6$ alkyl groups for $R_1$ functioned quite well in stabilizing the ABS foams. This functionality is quite unexpected because these same amine oxides are not surface active as the results of Example 2 demonstrate. Indeed, this result somewhat disproves the traditional notion that a foam stabilizer must be surface active in order to function properly.

EXAMPLE 5

As the results reported in Example 4 were unexpected, not all of the sets of runs had control tests included (a control test being conducted without the foam stabilizer). Thus, in order to confirm the results reported in Example 4, several amine oxides were re-synthesized and evaluated in the dishwashing test described above. In these tests, runs were included which had only the foam agent and no foam stabilizer (control runs). Also, runs were conducted wherein $R_3$, $R_4$ where hydroxybutyl (BO) groups. Finally, a conventional (identified as Standard in the Tables) amine oxide, which was dimethyl-dodecylamine (no ether linkage) was tested also. The results obtained appear below.

TABLE 10

| | | $R_3, R_4$ = Hydroxyethyl | | |
|---|---|---|---|---|
| | | No. of Plates Washed | | |
| Run No. | $R_1$ | ABS | ES | AOS |
| Control | | 10 | 12 | 14 |
| 1 | $C_4$ | 16 | 12 | 12 |
| 2 | $C_6$ | 16 | 8 | 14 |
| 3 | $C_8$ | 19 | 15 | 17 |
| 4 | $C_{10}$ | 19 | 15 | 17 |
| 5 | $C_{12}$ | 15 | 15 | 15 |
| 6 | $C_{14}$ | 11 | 12 | 9 |
| Standard | | 11 | 14 | 12 |

TABLE 11

| | $R_3, R_4$ = Methyl | |
|---|---|---|
| Run No. | $R_1$ | No. of Plates ABS |
| Control | | 10 |
| 1 | $C_4$ | 11 |
| 2 | $C_6$ | 12 |
| 3 | $C_8$ | 12 |
| 4 | $C_{10}$ | 8 |
| 5 | $C_{12}$ | 12 |

TABLE 12

| | $R_3, R_4$ = Hydroxybutyl | |
|---|---|---|
| Run No. | $R_1$ | No. of Plates ABS |
| Control | | 10 |
| 1 | $C_8$ | 13 |

These results confirm that with $R_3$ and $R_4$ being methyl groups the amine oxides did not adequately stabilize even the ABS foams. Also, the use of $R_3$, $R_4$ hydroxybutyl groups is shown to be acceptable. Further, the totally unexpected results using $R_3$, $R_4$ being $C_4$ and $C_6$ alkyl groups is confirmed beyond a doubt. Finally, the maximum chain length for $R_1$ being $C_{11}$ is confirmed for ABS foams. While the numbers of plates washed are not identical in Example 4 and this Example, the totally unexpected improvement in stabilizing ABS foams is demonstrated and confirmed in these Examples.

In order to more fully appreciate the results reported in Examples 4 and 5, several of the results reported in the Tables are displayed graphically. In the drawings is plotted $R_1$ chain length versus the number of plates difference between the various $R_1$ chain lengths. FIG. 1 corresponds to Table 7 of Example 4 and FIG. 2 corresponds to Table 10 of Example 5. Clearly, the unexpectedness and advantages of the present invention can be seen from the drawings.

We claim:

1. A foam stabilizer for stabilizing a foam containing an alkyl benzene sulfonate foaming agent, characterized by an amine oxide foam stabilizer represented by the following general structure

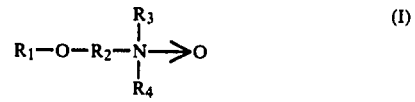

where,
$R_1$ is a $C_4$–$C_6$ alkyl group
$R_2$ is a $C_2$–$C_4$ alkylene group
$R_3$, $R_4$ each, independently, is a $C_1$–$C_4$ hydroxyalkyl group.

2. The foam stabilizer of claim 1 wherein $R_3$ and $R_4$ each, independently, is a $C_2$–$C_4$ hydroxyalkyl group.

3. The foam stabilizer of claim 1 wherein $R_2$ is a propylene group.

4. The foam stabilizer of claim 3 wherein $R_3$ and $R_4$ both are hydroxyethyl groups.

5. The foam stabilizer of claim 1 which is a mixture of amine oxides, each amine oxide having a different $R_1$ group.

6. The foam stabilizer of claim 1 wherein said alkyl benzene sulfonate foaming agent is dodecyl benzene sulfonate or tridecyl benzene sulfonate.

7. An alkyl benzene sulfonate foaming agent stabilized with a foam stabilizer, the improvement characterized by said foam stabilizer being an amine oxide foam stabilizer represented by the following general structure

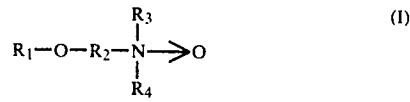

where,
$R_1$ is a $C_4$–$C_{11}$ alkyl group
$R_2$ is a $C_2$–$C_4$ alkylene group
$R_3$, $R_4$ each, independently, is a $C_1$–$C_4$ hydroxyalkyl group.

8. The stabilized alkyl benzene sulfonate of claim 7 wherein $R_3$ and $R_4$ each, independently, is a $C_2$–$C_4$ hydroxyalkyl group.

9. The stabilized alkyl benzene sulfonate of claim 7 wherein $R_2$ is a propylene group.

10. The stabilized alkyl benzene sulfonate of claim 9 wherein $R_3$ and $R_4$ both are hydroxyethyl groups.

11. The stabilized alkyl benzene sulfonate of claim 10 wherein $R_1$ is a $C_8$–$C_{11}$ alkyl group.

12. The stabilized alkyl benzene sulfonate of claim 7 which is a mixture of amine oxides, each amine oxide having a different $R_1$ group.

13. The stabilized alkyl benzene sulfonate of claim 7 or claim 11 wherein said alkyl benzene sulfonate foaming agent is dodecyl benzene sulfonate or tridecyl benzene sulfonate.

14. The stabilized alkyl benzene sulfonate of claim 7 wherein $R_1$ is a $C_4$–$C_6$ alkyl group.

15. In a foamable composition which is soluble in water, said composition including an alkyl benzene sulfonate foaming agent, the improvement characterized by an amine oxide foam stabilizer represented by the following general structure:

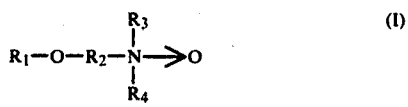

where,
$R_1$ is a $C_4$–$C_{11}$ alkyl group
$R_2$ is a $C_2$–$C_4$ alkylene group
$R_3$, $R_4$ each, independently, is a $C_1$–$C_4$ hydroxyalkyl group.

16. The foamable composition of claim 15 wherein $R_3$ and $R_4$ each, independently, is a $C_2$–$C_4$ hydroxyalkyl group.

17. The foamable composition of claim 15 wherein $R_2$ is a propylene group.

18. The foamable composition of claim 17 wherein $R_3$ and $R_4$ both are hydroxyethyl groups.

19. The foamable composition of claim 18 wherein $R_1$ is a $C_8$–$C_{11}$ alkyl group.

20. The foamable composition of claim 15 which is a mixture of amine oxides, each amine oxide having a different $R_1$ group.

21. The foamable composition of claim 15 or claim 19 wherein said alkyl benzene sulfonate foaming agent is dodecyl benzene sulfonate or tridecyl benzene sulfonate.

22. The foamable composition of claim 15 wherein $R_1$ is a $C_4$–$C_6$ alkyl group.

23. The foamable composition of claim 15 or claim 19 which is a liquid, a powder, or a gel.

24. The foamable composition of claim 15 which is a liquid composition for cleaning dishes, clothes, hair, or skin.

25. The foamable composition of claim 15 which is a powder for cleaning dishes or clothes.

26. The foamable composition of claim 15 which is gel for cleaning dishes, clothes, hair or skin.

27. In a process for making a water-soluble foamable composition which includes an alkyl benzene sulfonate foaming agent, the improvement characterized by adding to said composition a foam-stabilizing effective proportion of an amine oxide foam stabilizer represented by the following general structure:

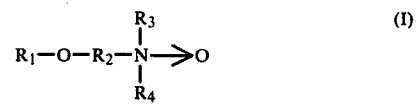

where,
$R_1$ is a $C_4$–$C_{11}$ alkyl group
$R_2$ is a $C_2$–$C_4$ alkylene group
$R_3$, $R_4$ each, independently, is a $C_1$–$C_4$ hydroxyalkyl group.

28. The process of claim 27 wherein $R_3$ and $R_4$ each, independently, is a $C_2$–$C_4$ hydroxyalkyl group.

29. The process of claim 27 wherein $R_2$ is a propylene group.

30. The process of claim 29 wherein $R_3$ and $R_4$ both are hydroxyethyl groups.

31. The process of claim 30 wherein $R_1$ is a $C_8$–$C_{11}$ alkyl group.

32. The process of claim 27 wherein $R_1$ is a $C_4$–$C_6$ alkyl group.

33. The process of claim 27 wherein said foam stabilizer is a mixture of amine oxides, each amine oxide having a different $R_1$ group.

34. The process of claim 27 or claim 31 wherein said alkyl benzene sulfonate foaming agent is dodecyl benzene sulfonate or tridecyl benzene sulfonate.

35. The process of claim 27 or claim 31 wherein said foamable composition is a liquid, a powder, or a gel.

* * * * *